(12) United States Patent
Coiseur (10) Patent No.: US 11,438,499 B2
(45) Date of Patent: *Sep. 6, 2022

(54) SCIALYTIC LIGHT NAVIGATION (71) Applicant: MedTech S.A., Montpellier (FR)

(72) Inventor: Florian Coiseur, Lattes (FR)

(73) Assignee: MedTech S.A., Montpellier (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/232,756

(22) Filed: Apr. 16, 2021

(65) Prior Publication Data
US 2021/0289127 A1 Sep. 16, 2021

Related U.S. Application Data

(63) Continuation of application No. 16/225,617, filed on Dec. 19, 2018, now Pat. No. 10,999,493.

(Continued)

(51) Int. Cl.
*H04N 5/232* (2006.01)
*H04N 5/235* (2006.01)
(Continued)

(52) U.S. Cl.
CPC ......... *H04N 5/23219* (2013.01); *A61B 34/20* (2016.02); *A61B 90/30* (2016.02); *G06T 7/0012* (2013.01); *G06V 10/242* (2022.01); *H04N 5/2354* (2013.01); *H04N 5/247* (2013.01); *H04N 5/33* (2013.01); *H04N 13/25* (2018.05); *A61B 90/50* (2016.02); *A61B 2034/2055* (2016.02); *A61B 2034/2057* (2016.02);
(Continued)

(58) Field of Classification Search
None
See application file for complete search history.

(56) References Cited

U.S. PATENT DOCUMENTS 6,434,329 B1 * 8/2002 Dube .................. F16M 11/126
128/897
6,633,328 B1 * 10/2003 Byrd ..................... H04N 7/183
348/143

(Continued)

FOREIGN PATENT DOCUMENTS

CN     102743227 A    10/2012
CN     109998677 A    7/2019
WO     WO-0069354 A1  11/2000

OTHER PUBLICATIONS

"U.S. Appl. No. 16/225,617, Final Office Action dated Aug. 17, 2020", 18 pgs.

(Continued)

*Primary Examiner* — Stuart D Bennett
(74) *Attorney, Agent, or Firm* — Schwegman Lundberg & Woessner, P.A.

(57) ABSTRACT

A system and method for tracking an object within a surgical field are described. A system may include a lighting component to illuminate a surgical field, and a camera device to capture an image of a tracked device within the surgical field. The system may include a rotational component configured to rotate with respect to the lighting component. The camera device may couple to the rotational component to rotate with respect to the lighting component, such as in response to an obstruction of a tracked object being detected.

20 Claims, 7 Drawing Sheets

Related U.S. Application Data (60) Provisional application No. 62/609,893, filed on Dec. 22, 2017.

(51) Int. Cl.

| | | |
|---|---|---|
| *H04N 5/247* | (2006.01) | |
| *H04N 5/33* | (2006.01) | |
| *H04N 13/25* | (2018.01) | |
| *G06T 7/00* | (2017.01) | |
| *A61B 34/20* | (2016.01) | |
| *A61B 90/30* | (2016.01) | |
| *G06V 10/24* | (2022.01) | |
| *A61B 90/00* | (2016.01) | |
| *F21W 131/205* | (2006.01) | |
| *A61B 90/50* | (2016.01) | |

(52) U.S. Cl.
CPC ............... *A61B 2034/2065* (2016.02); *A61B 2090/3937* (2016.02); *F21W 2131/205* (2013.01); *G06T 2207/10048* (2013.01); *G06T 2207/30204* (2013.01); *G06T 2207/30244* (2013.01); *G06T 2210/41* (2013.01); *Y10S 362/804* (2013.01)

(56) References Cited

U.S. PATENT DOCUMENTS

| | | | |
|---|---|---|---|
| 8,882,777 | B2 | 11/2014 | Heavener |
| 10,999,493 | B2 | 5/2021 | Coiseur |
| 2003/0164953 | A1* | 9/2003 | Bauch .................... A61B 90/30 356/611 |
| 2006/0142657 | A1 | 6/2006 | Quaid et al. |
| 2007/0014567 | A1 | 1/2007 | Rossner et al. |
| 2007/0156157 | A1 | 7/2007 | Nahum et al. |
| 2011/0037840 | A1 | 2/2011 | Hiltl et al. |
| 2012/0209117 | A1 | 8/2012 | Mozes et al. |
| 2015/0300816 | A1 | 10/2015 | Yang et al. |
| 2017/0071685 | A1 | 3/2017 | Crawford et al. |
| 2017/0167702 | A1 | 6/2017 | Mariampillai et al. |
| 2019/0199915 | A1 | 6/2019 | Coiseur |

OTHER PUBLICATIONS

"U.S. Appl. No. 16/225,617, Non Final Office Action dated Apr. 15, 2020", 16 pgs.

"U.S. Appl. No. 16/225,617, Notice of Allowance dated Jan. 6, 2021", 15 pgs.

"U.S. Appl. No. 16/225,617, Response filed Jul. 15, 2020 to Non Final Office Action dated Apr. 15, 2020", 8 pgs.

"U.S. Appl. No. 16/225,617, Response filed Dec. 17, 2020 to Final Office Action dated Aug. 17, 2020", 7 pgs.

"European Application Serial No. 18215508.5, Communication Pursuant to Article 94(3) EPC dated Sep. 8, 2020", 4 pgs.

"European Application Serial No. 18215508.5, Extended European Search Report dated May 15, 2019", 6 pgs.

"European Application Serial No. 18215508.5, Response filed Dec. 20, 2019 to Extended European Search Report dated May 15, 2019", 15 pgs.

U.S. Appl. No. 16/225,617 U.S. Pat. No. 10,999,493, Dec. 19, 2018, Scialytic Light Navigation.

"Chinese Application Serial No. 201811579765.X, Office Action dated Jul. 5, 2021", W/English Translation, 16 pgs.

"Chinese Application Serial No. 201811579765.X, Response filed Oct. 9, 2021 to Office Action dated Jul. 5, 2021", w/ English claims, 14 pgs.

* cited by examiner

SCIALYTIC LIGHT NAVIGATION

CLAIM OF PRIORITY

This application is a continuation of U.S. patent application Ser. No. 16/225,617, filed on Dec. 19, 2018, which claims the benefit of U.S. Provisional Patent Application Ser. No. 62/609,893, filed on Dec. 22, 2017, the benefit of priority of each of which is claimed hereby, and each of which is incorporated by reference herein in its entirety.

BACKGROUND

Cameras, object recognition technology, and tracking systems may be utilized to assist with surgical operations. This technology may be used to locate surgical instruments or track the location of patient operational points. Previous systems have relied on a static camera device. In the surgical field, object recognition and object tracking with a static camera device proves difficult, such as when a surgeon, surgical assistant, robotic device, or other object blocks the static camera device from detecting a tracked object. When the tracked object is not detected, aspects of a surgical procedure may need to stop, causing delays and initiation steps to be repeated. Some camera devices are located on moving carts, but still must be static while tracking objects during a procedure, and thus suffer from the same issues as other static cameras.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Systems and methods for using a camera device to track objects within a surgical field that is illuminated by a lighting device are described herein. The systems and methods herein may include a camera device coupled to a lighting device, such as via an arm. The camera device may track objects using optical navigation. Optical navigation systems rely on an unobstructed line of sight between tracking elements and sensors (e.g., within the camera device) that receive tracking signals from the tracking elements. When the line of sight is obstructed (by a surgeon's arm or a robotic arm for example), tracking signals being transmitted from the tracking element may not be received by the sensors or the camera device. As a result, errors may occur in tracking the objects. In an example where obstruction occurs, the optical navigation system may be discontinued, the surgical procedure stopped, or an error message may be conveyed to the surgeon. These changes may be temporary, such as until the line of sight returns or the system is reset.

The systems and methods herein describe a navigation system that quickly identifies line of sight issues so that obstructions may be resolved without significant delay. The navigation systems and methods described herein may improve a field of view or reduce possible errors associated with Obstruction along a line of sight between a tracking element and a sensor/camera device.

In an example, a system or method may track objects within a surgical field via a motorized navigation camera coupled to a scialytic light. A scialytic light, as discussed herein may be used as an example type of light for use within a surgical field, such as a light or plurality of lights configured to reduce or remove shadows within the surgical field. The motorized navigation camera may include a camera device, such as a depth camera, field of view camera, single camera, dual camera, plurality of cameras, or the like, which may be moveable, such as with a motor or by hand (e.g., with respect to a light). In another example, multiple cameras (e.g., camera devices, navigation cameras, depth cameras, etc.) may be used, such as using two or more camera devices coupled to a light (e.g., on opposite sides of the light, or having different lines of sight).

In an example, a scialytic light may be coupled to a camera device, and both may be communicatively coupled to a processor. The processor may control the scialytic light or the camera (or a motor to rotate the camera). When controlling the scialytic light, the processor may cause the scialytic light to display a special illumination mode (e.g., blink, change color, etc.) to indicate that there is a line of sight error with the camera device. Alerting the surgeon using the special illumination mode may allow the surgeon to avoid needing to look at a screen outside the surgical field.

A camera device used for tracking within a surgical field may comprise a camera, or a plurality of cameras communicatively coupled to a computer image analysis system. By utilizing the camera mesh and the computer image analysis system, objects involved in the surgical procedure may be tracked, such as instruments (e.g., scalpel, implant insertion tools), a body part, or an implant. Tracking an object is not limited to a tool or instrument used by the surgeon. The tracked object may include a body part, such as a leg or hand, the location of an incision, the positioning of a bone inside the body part, or the location of an organ within the patient. In an example, the camera device may track multiple objects simultaneously.

The camera device may be configured in many ways for tracking an object or an optical tracker. The camera device may include a depth camera. The camera device may use infrared light to track an object or an optical tracker. In this example, the camera device may be located at a fixed position within a surgical field during a procedure (although, as described below, the camera may rotate when an obstruction is detected or predicted). In an example, the camera devices may include stereoscopic cameras (e.g., two cameras within a single housing).

The tracking data imaged by a camera device or collected by an image processing system (e.g., using a processor) may be used to determine a position and an orientation of a tracked object within a virtual three-dimensional coordinate system (e.g., within the surgical field). The tracking data may include the position and direction of the camera device. The image processing system may output the position and the orientation of the tracked object. The output data may include coordinates in a virtual three-dimensional coordinate system. The output may include one or more of the captured synchronized images that includes the tracked object. Using the tracking data, a processor may determine that a tracked object is obstructed or may predict that a tracked object is going to be or likely to be obstructed in the near future (e.g., within a second, within a few frames, etc.).

Robotics have become a useful tool for assisting the surgeon in the surgical field. A robotic device may assist in the surgical field performing tasks such as biopsies, electrode implantation for functional procedures (e.g., stimulation of the cerebral cortex, deep brain stimulation), open skull surgical procedures, endoscopic interventions, other "key-hole" procedures, arthroplasty procedures, such as total or partial knee replacement, hip replacement, shoulder implant procedures, or the like. In an example, a surgical procedure may use a surgical robot. The surgical robot may include a tracker, which a tracking system may use to determine a relative location of the surgical robot within a coordinate system or a surgical field. The surgical robot may have a different coordinate system or tracking system (e.g., using known movements of the surgical robot to keep track of an end effector of a robotic arm of the surgical robot, which may include using sensors, such as a gyroscope, magnetoscope, accelerometer, etc.). In an example, a processor may be used to coordinate or translate information from the surgical robot coordinate or tracking system with a camera-based tracking system.

An optical tracker may be attached to an object for tracking the object in an optical tracking system, in accordance with some examples. The optical tracker may include one or multiple reflective components or an active marker such as a light emitting diode (LED), which may be at a set position on the optical tracker (e.g., relative to one another). The optical tracker may be attached to an object in the surgical field such as an instrument or a body part (e.g., a bone). The position and orientation of the object relative to the object tracker may be set and recorded such that an optical tracking system may know the position and orientation of the object by determining the position and orientation of the optical tracker (e.g., using a camera device to capture an image or information about the optical tracker). The position and orientation of the optical tracker may be determined by detecting the one or multiple reflective components and correlating the detected reflective component positioning to the known relative positioning of the multiple reflective components on the optical tracker.

Figure 1:
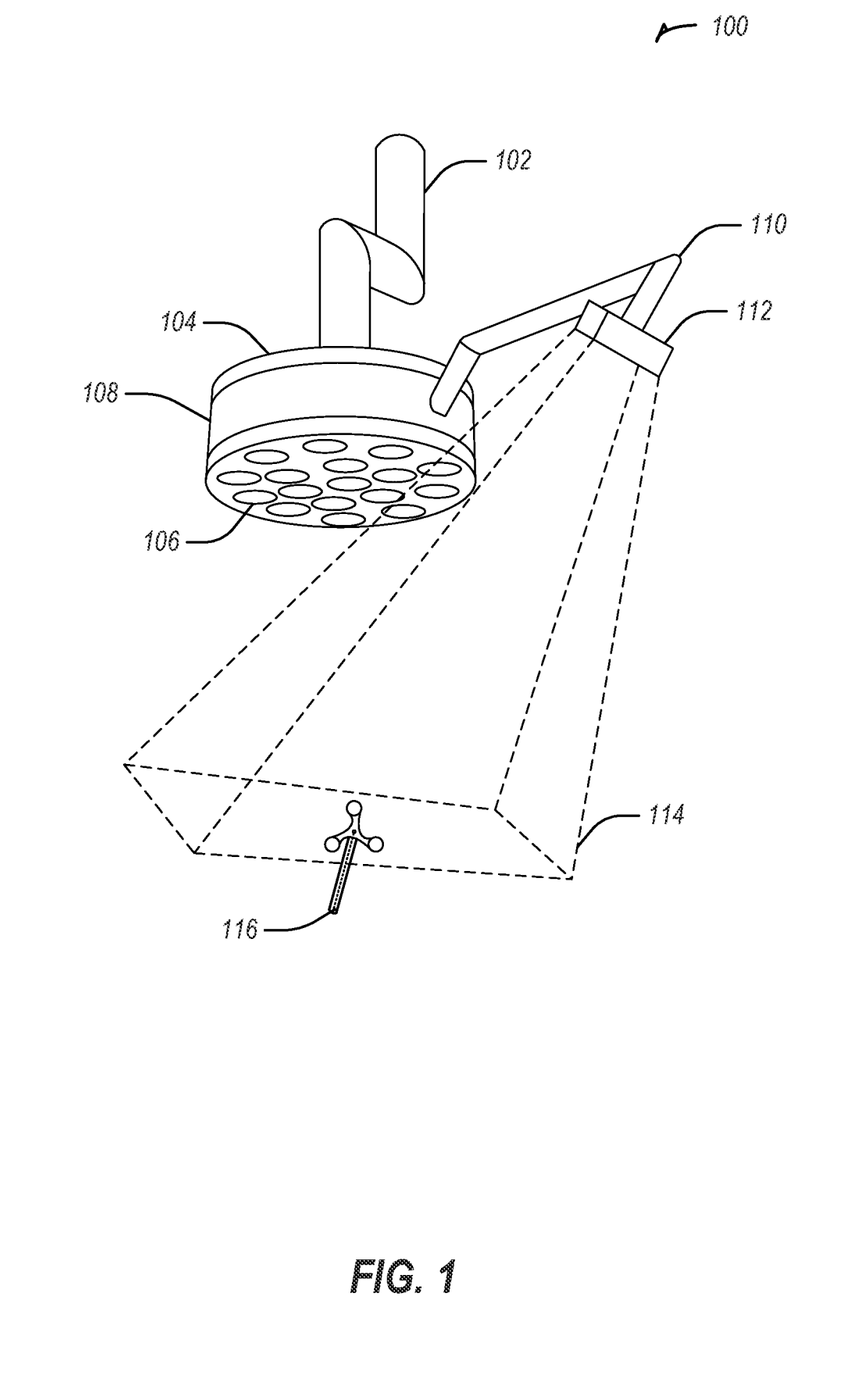
FIG. 1 illustrates a camera and light system in accordance with some embodiments.

FIG. 1 illustrates a camera and light system 100 in accordance with some embodiments. The camera and light system 100 may be used in a surgical field for lighting, tracking objects, or image collection. The camera and light system 100 includes a lighting component 106, which may include a plurality of lights. The lighting component 106 may be coupled to a rotational component 108. The rotational component 108 is coupled to a camera attachment 110 in the example shown in FIG. 1. The camera attachment 110 includes a camera device 112 at a distal end. In another example, not shown, the camera device 112 may be coupled directly to the rotational component 108. In either case, the camera device 112 is coupled to the lighting component 106 via the rotational component 108, the rotational component 108 configured to rotate the camera device 112 with respect to the lighting component 106. Rotating the camera device 112 with respect to the lighting component 106 may include rotating the camera device 112 without moving or rotating the lighting component 106. In an example, rotating the camera device 112 may include rotating in response to a parameter defining a line of sight (e.g., to a marker) or line of sight obstruction (e.g., a line of sight quality parameter). The rotational component 108 may be motorized, such that the rotational component 108 may be controlled to change the field of view 114 by rotating the camera device 112.

The camera and light system 100 may include a housing 104 for the lighting component 106, which may be coupled to a mounted arm 102. In an example, the mounted arm 102 may in turn be coupled to a fixed portion of a surgical field (e.g., a ceiling of a surgical room). The camera device 112 may rotate with respect to the housing 104, the lighting component 106, the mounted arm 102, or the fixed portion of the surgical field. In another example, the mounted arm 102 may be fixed to a mobile cart (which may be locked in a particular location during use).

The mounted arm 102 may be sufficiently rigid to prevent movement of the housing 104 or the lighting component 106 during rotation of the camera device 112. In an example, the mounted arm 102 may include one or more encoders (for position determination) in one or more joints of the mounted arm 102 to determine the position of the housing 104, the lighting component 106, the rotational component 108, or the camera device 112. The housing 104 may include a handle for housing placement/adjustment by the surgeon. When surgeon has placed the lighting component 106 in position (e.g., by using the handle), positions of the lighting component 106 and the camera device 112 may be known by way of mounted ceiling arm joint 102 encoders and system design (e.g., known lengths or sizes of the components of the camera and light system 100). The handle may have a button to active or shut off a brake in one or more joints of the mounted arm 102 (e.g., to stop the mounted arm 102 from moving or allow it to move). This button may permit the mounted arm 102 to move when and where the surgeon wants and stop the mounted arm 102 (by activating the brakes) to prevent any unintentional movements during surgery or movements caused by rotational movement of the camera device 112.

The camera device 112 may have a field of view 114, for example to track objects within a surgical field. The lighting component 106 may be used to illuminate aspects of the surgical field, such as within the field of view 114. The camera device 112 may track an object 116 within the field of view 114. A line of sight (e.g., a line within the field of view 114) from the camera device 112 to the tracked object 116 may become obstructed (e.g., partially or totally). In accordance with a determination that the line of sight is obstructed or is going to become obstructed, the camera device 112 may rotate (changing the field of view 114 and the line of sight) via the rotational component 108 to obtain a clear line of sight to the tracked object 116.

In an example, an obstruction may be detected for the tracked object 116 when one or more aspects of the tracked object 116 are undetectable by the camera device 112. For example, the tracked object 116 may have a plurality of reflective components for infrared detection by the camera device 112. When one or more of the plurality of reflective components or one or more active components, such as an LED, are undetectable by the camera device 112, the camera device 112 may rotate to reobtain a line of sight that allows the camera device 112 to detect the plurality of reflective components.

In an example, to predict that the line of sight is going to become obstructed, a processor (e.g., at a computing device, at a mobile device, within the camera and light system 100, within the camera device 112, in a remote device, or the like) may determine from previous frames (two or more) that an object (e.g., an instrument, the surgeon, a surgical assistant, a robotic arm, etc.) is moving into a line of sight between the camera device 112 and the tracked object 116 or a portion of the tracked object 116. For example, movement of the object may be detected in a direction to the line of sight from a first frame to a second frame of the previous frames. In response to detecting the movement of the object towards the line of sight, the camera device 112 may move to a new location such that a new line of sight from the camera device 112 to the tracked object 116 is not predicted to be obstructed by the object.

In another example, when the object that is going to obstruct the tracked object 116 is a robotic arm or other computer controlled device (i.e., an autonomous device that moves according to a controller), a robotic controller or other controller may identify that movement of the object is going to obstruct the line of sight between the camera device 112 and the tracked object 116. This information may be communicated to the camera device 112 to instruct the camera device 112 to rotate before the tracked object 116 is obstructed. For example, a robotic arm may be instructed by a robotic controller to move to a set of coordinates. Knowing the dimensions of the robotic arm, the previous location of the robotic arm and the coordinate, the robotic controller may determine whether the robotic arm will intersect the line of sight (e.g., using information from the camera device 112 about the location of the tracked object 116 and the location of the camera device 112). In another example, the robotic controller may send the coordinates to the camera device 112 or a computing device to determine whether the robotic arm will intersect the line of sight. The camera device 112 may output coordinates of a location of the tracked object 116 in a first coordinate system, as well as a location within the first coordinate system of the camera device 112 itself (e.g., at the origin, or including a rotational component). The robotic arm coordinates may be output in a second coordinate system. A processor may convert between the first and second coordinate systems to determine whether the robotic arm will intersect with the line of sight. In an example, the camera device 112 may include a wired or wireless communication component to communicate coordinates, images, tracked information or the like to the processor or other device. A wired connection may connect via the mounted arm 102. A wireless connection may include a transceiver, which may be located within the camera device 112 or the housing 104.

In an example, the lighting component 106 may be used to indicate to a user (e.g., a surgeon) that the line of sight between the camera device 112 and the tracked object 116 is obstructed or for other errors. The indication may include a flash of the lighting component 106, a change in light color, a pulse, or the like. The indication may cause a robotic arm to stop moving, move out of a line of sight or the field of view 114, or the like.

The camera device 112 may use infrared (IR) light sensors with passive reflective spheres (e.g., on the tracked object 116) for tool, anatomy, or robotic tracking (e.g., position and orientation). In an example, other tracking technologies may be used, such as structured light or time of flight to track the object 116, such as by creating a 3D model. In an example, the camera device 112 may move around the lighting component 106 by via motorized link when the signal between the tracked object 116 and the camera device 112 is lost, to look for and retrieve a signal from the tracked object 116 to avoid navigation interruption.

In an example, the camera device 112 may rotate in a single direction, moving as fast as possible to find the tracked object (e.g., via a motor within the rotational component 108). In another example, the camera device 112 may rotate in either direction (e.g., to a closest location without an obstructed view). In yet another example, the camera device 112 may rotate continuously, such that the camera device 112 always has a clear line of sight to the tracked object 116 at least once per rotation. The rotational speed may be configured such that the camera accurately tracks the object 116 even with only one clear line of sight (e.g., for imaging or sensing) once per rotation. The rotational speed may be aligned with a shutter speed or detection speed such that clear images may be taken at predetermined or specified locations each rotation. For example, when the camera device 112 takes 60 images per second and the camera device 112 needs two images per second to accurately track the object 116, the rotation speed may be set to cause the camera device 112 to rotate twice per second, giving 30 images per rotation, with at least two images not obstructed per second. The speed may be varied based on the number of images taken per second and the number of clear line of sight images needed per second. In reality, the camera device 112 is likely to have far more than one unobstructed line of sight per rotation, so in these examples the camera device 112 may obtain many more usable location images per rotation.

The camera mounting system (e.g., rotational component 108, camera attachment 110, etc.) may be calibrated so that the physical position of the camera device 112 is known within a virtual coordinate system or the surgical field at any rotational position. In some examples, the rotational component 108 may include encoders or other rotational position sensors to provide an accurate rotational location of the camera attachment 110 and camera device 112. With the ability to accurate track rotational position, the exact field of view, such as field of view 114, may be calculated at any point in the rotation of the camera device 112. In some examples, additional fixed tracking markers can be positioned though out the surgical field to further assist in transforming the virtual coordinate system between rotational positions of camera device 112. The fixed tracking markers (not specifically shown in FIG. 1) may be mounted to a surgical table or other immovable objects within the surgical field. The fixed tracking markers may be utilized to account for any movement of the tracked object 116 between positional movements of the camera device 112. In other examples, movements of the camera device 112 are sufficient fast to make any movement of the tracked object 116 negligible between frames. In yet other examples, tracked instruments and/or robotic arms can be utilized to assist in transforming the virtual coordinate system to the new camera position. For example, in scenarios utilizing a robotic arm, a portion of the robot can include tracking marker, which may be tracked by the camera device 112 as well as having a known fixed relationship to the robotic arm. The known fixed relationship to the robotic arm can be utilized to validate or calculate any interim movement of the tracked object 116 during movement of the camera device 112 from one position to a second position.

The camera attachment 110 may be rigid or may be moveable (e.g., adjustable in length, angle, or orientation to the lighting component 106), but during operation it may be fixed. The camera attachment 110 or the camera device 112 may be calibrated such that the field of view 114 includes an entire surgical field or a desired portion of the surgical field. In an example, the moveable arm (e.g., the camera attachment 110) may include an anthropomorphic-like robotic arm having one or more encoders in one or more joints to determine the position of the camera device 112 relative to the rotational component 108.

Figure 2:
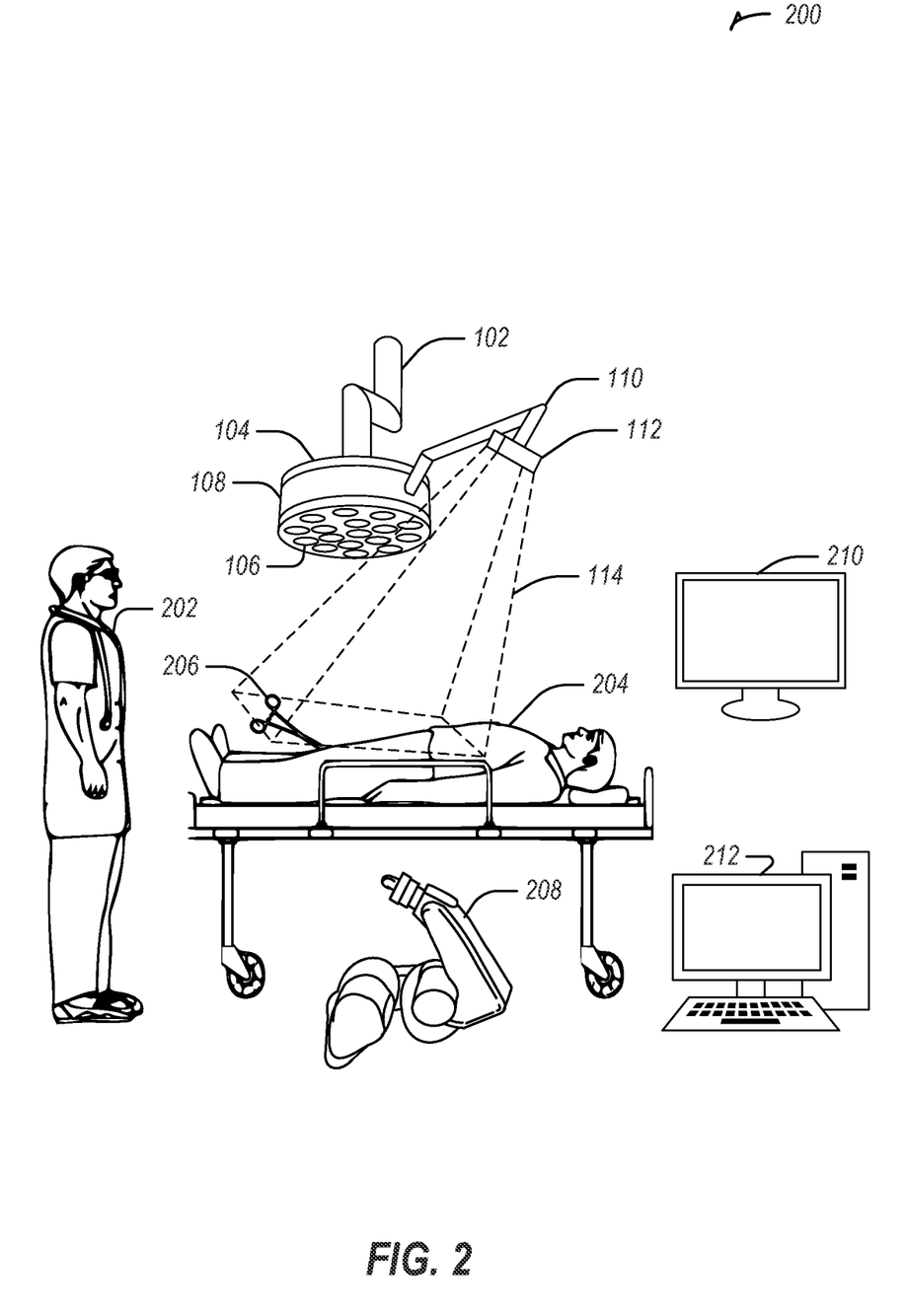
FIG. 2 illustrates a surgical procedure setup including a camera and light system in accordance with some embodiments.

FIG. 2 illustrates a surgical procedure setup 200 including the camera and light system 100 in accordance with some embodiments. The surgical procedure setup 200 illustrates a surgeon 202, a patient 204, a surgical instrument 206 (which may be an example of an object tracked by the camera and light system 100), a robotic arm 208, a display device 210, and a computing device 212, each of which may be included or omitted in a given surgical procedure. In an example, the robotic arm 208 may be tracked by the camera and light system 100. As shown in FIG. 2, the field of view 114 may be less than an entire surgical field. The camera device 112 may rotate as described above, for example in response to detecting an obstruction or predicted obstruction of a line of sight from the camera device 112 to the surgical instrument 206 (or other tracked object), such as an obstruction by the surgeon 202, the robotic arm 208, or the like.

The display device 210 may be used to display information for the surgical procedure, which may include tracking information from the camera device 112. In an example, the display device may show an alert, such as when a line of sight to the surgical instrument 206, which may be a tracked object, from the camera device 112 is obstructed. The computing device 212 may be used to determine tracking information, compare or convert coordinates e.g., coordinates of a location of a portion of the robotic arm within a first coordinate system and coordinates of a location of the surgical instrument 206 within a second coordinate system).

The robotic arm 208 may be used by the surgeon 202 to perform a surgical procedure, such as on a knee joint of the patient 204. The robotic arm 208 may use tracking information from the camera device 112, which may track a bone of the patient 204 (e.g., a femur or a tibia) or the surgical instrument 206, or another device, tool, or aspect of patient anatomy to perform the surgical procedure.

As noted above, fixed tracking markers may, in some examples, be located throughout the surgical field. In this example, the fixed tracking markers may be affixed to the surgical table supporting the patient 204. Further, fixed tracking markers may be affixed to portions of the robot 208. In yet other examples, fixed tracking markers may be affixed to portions of the patient not directly involved in the surgery and not likely to be moved.

Figure 3:
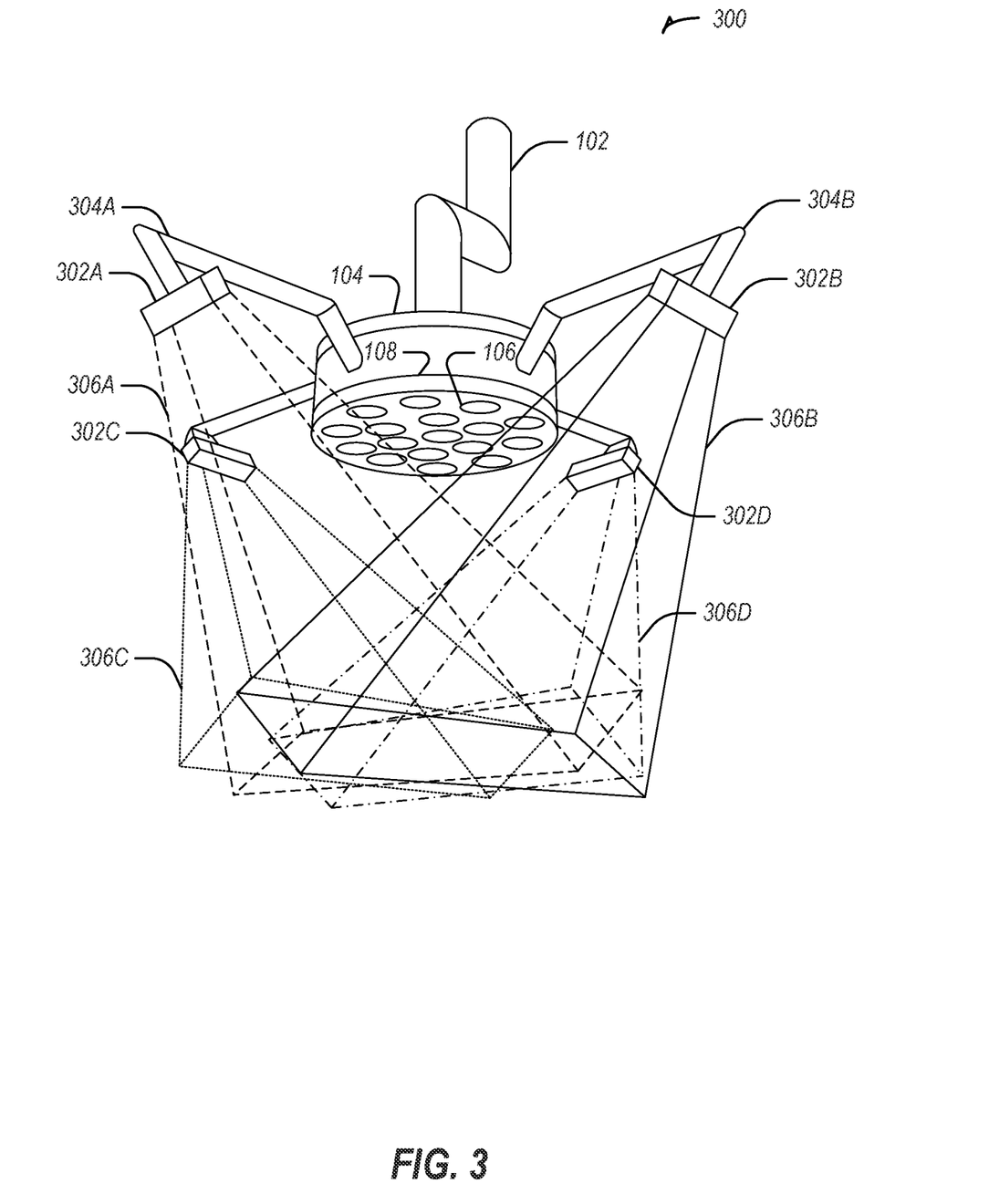
FIG. 3 illustrates a multiple camera and light system in accordance with some embodiments.

FIG. 3 illustrates a multiple camera and light system 300 in accordance with some embodiments. The multiple camera and light system 300 shown in FIG. 3 includes four camera devices 302A-302D, although two or three camera devices may be used, or more than four camera devices may be used. The multiple camera and light system 300 uses a plurality of camera devices 302A-302D for a plurality of field of views 306A-306D. In an example, the multiple camera and light system 300 may include components similar to those of FIG. 1, including a housing 104, a lighting component 106, a rotational component 108, or a support arm 102. The camera devices 302A-302D may be connected to the housing 104 or the lighting component 106 via camera attachments 304A-304D, respectively.

In an example, the multiple camera and light system 300 may rotate the camera devices 302A-302D, such as in response to an obstruction detected or predicted in a line of sight to a tracked object. In an example, the multiple camera and light system 300 may track one or multiple objects. Based on the number of objects tracked, different techniques may be used to adjust rotation of the camera devices 302A-302D. In an example, when a single object is tracked, the multiple camera and light system 300 may rotate only when all respective lines of sight from the camera devices 302A-302D to the single tracked object are obstructed or predicted to be obstructed, when a plurality of lines of sight are obstructed to a single tracked device, or when at least one line of sight is obstructed. For example, the camera devices 302A-302D may be rotated in different techniques when only one line of sight is obstructed, or in other examples, when two lines of sight, three lines of sight, or all four lines of sight are obstructed. Similarly, when two, three, or more than four camera devices are used, techniques may be used to rotate the camera devices when one, two, three, four, or more lines of sights are obstructed. In an example, the multiple camera and light system 300 may decrease the number of possibilities of line of sight issues by covering the largest field of view as possible (e.g., 360° in a best case). Even in this case, rotational movement may occur when all lines of sight are obstructed to retrieve at least one line of sight permitting tracking.

In another example, a lead camera device 302A may be designated when a single object is tracked. In this example, when a line of sight is obstructed or predicted to be obstructed, tracking may be switched to one of the backup camera devices 302B-D, such as depending on which of the backup camera devices 302B-D have a best line of sight (e.g., least obstructed, and may include a specified order when no obstructions are present or predicted). The camera devices 302A-302D may be rotated such that the lead camera device 302A regains a line of sight to the single tracked object, or the backup camera 302B with a clear line of sight may be designated a new lead camera device. In this example, the backup camera devices 302B-D may operate with different settings, such as lower power, taking fewer images or sensor collections per time period, lower resolution for image capture, taking images or collecting sensor data, but not sending it or not processing it, or the like. Once activated to lead camera, the settings may be restored to ideal operating properties.

In an example, more than one object may be tracked within a surgical field. When tracking more than one object, the camera devices 302A-302D may be rotated when any line of sight to any of the tracked objects is obstructed or predicted to be obstructed. For example, tracking three objects in FIG. 3 would have twelve sight lines (one from each camera device to each tracked object), and when any of the twelve are obstructed, the camera devices 302A-302D are rotated.

In another example, the camera devices 302A-302D may be rotated when all lines of sight to any of the tracked objects are obstructed or predicted to be obstructed. For example, tracking three objects in FIG. 3 would have twelve sight lines, and when all four sight lines to a single tracked object are obstructed, the camera devices 302A-302D are rotated. Thus in this example, multiple sight lines (up to three per tracked object) may be obstructed without rotation, so long as at least one sight line per tracked object is not obstructed. In this example, not all tracked objects may be visible to all camera devices or to even a single camera device, but each tracked object is visible to the multiple camera and light system 300 because at least one line of sight to the tracked object from at least one of the camera devices is clear.

In yet another example, the camera devices 302A-302D may be rotated when more than one line of sight from one of the camera devices 302A-302D to a tracked object are obstructed or predicted to be obstructed. For example, when two or three lines of sight to an object are obstructed, the camera devices 302A-302D may be rotated. The examples related to FIG. 3 have been presented with three tracked objects and four camera devices, but they may be applied to two tracked objects, or more than three tracked objects, two or three camera devices, or more than four camera devices.

Figure 4:
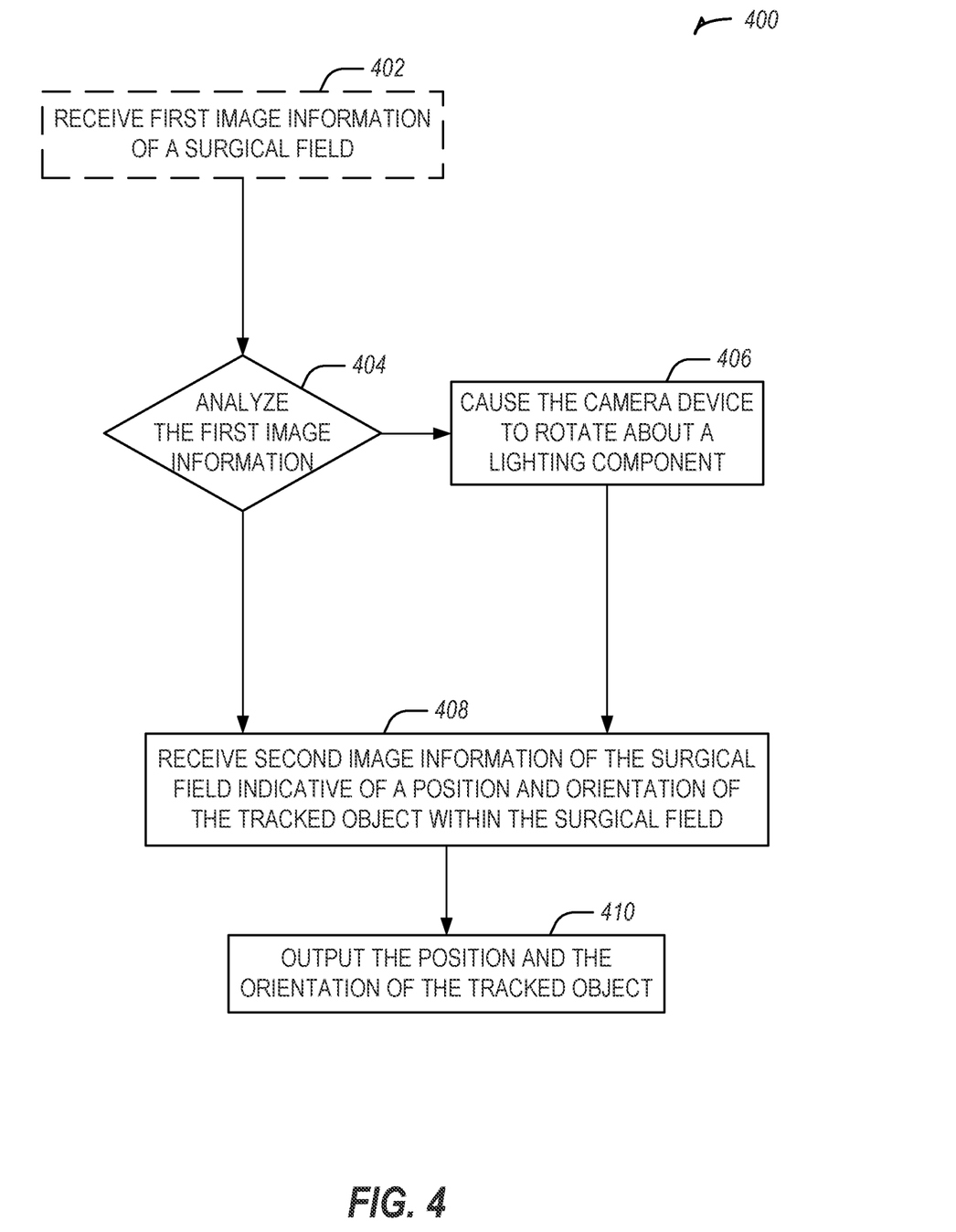
FIG. 4 illustrates a flowchart illustrating a technique for using a camera and light system in accordance with some embodiments.

FIG. 4 illustrates a flowchart illustrating a technique 400 for using a camera and light system in accordance with some embodiments. The technique 400 includes an optional operation 402 to receive, for example from a camera device, first image information of the surgical field.

The technique 400 includes a decision operation 404 to analyze the first image information. Decision operation 404 may include determining whether a sight line from the camera device to a tracked object is obstructed. Optionally, the decision operation 404 may include predicting that a sight line is going to become obstructed by calculating a trajectory of an object likely to obstruct the sight line from previous images or from information received about future coordinates of a robotic arm. In response to determining that the sight line is at least partially obstructed, the technique 400 may proceed to an operation 406. Operation 406 includes causing the camera device to rotate about a lighting component. After rotating the camera device, the technique may continue to operation 408. In another example, such as in response to determining that the sight line is not obstructed, the technique 400 may continue to operation 408. Rotating the camera device may include rotating the camera device to a location where the tracked object is not obstructed in a second sight line to the camera device without the lighting component rotating, for example using an external device coupled to the system or another camera coupled to the system to determine the location where the tracked object is not obstructed. In an example, rotating the camera device includes rotating the camera device in response to determining that the tracked object is at least partially obstructed from the sight line of the camera device and a second sight line of a second camera device. In another example, the camera device may be rotated by activating a motor to cause a rotational component coupled to the light component (e.g., a proximal end of the rotational component is affixed to the lighting component and a distal end of the rotational component is affixed to the camera device) to rotate. In yet another example, the camera device may be constantly rotated about the lighting component.

The technique 400 includes an operation 408 to receive second image information (e.g., from the camera device) of the surgical field indicative of a position and orientation of the tracked object within the surgical field. In an example, the position and orientation of the tracked object may be determined from the first image information. In an example, operation 408 may use a parameter defining quality of the line of sight (e.g., degree of obstruction) to determine whether rotation is needed.

The technique 400 includes an operation 410 to output the position and the orientation of the tracked object. The technique 400 may include flashing a light of the lighting component in response to detecting the at least partial obstruction. In an example, the flash or indicating portion of the lighting component may be performed with visual wavelengths, while the camera device may be adapted to capture non-visible wavelengths (e.g., infrared). The visible flash alerting the surgeon and the non-visible light used by the camera devices allows a camera and light system using the technique 400 to include lighting based signaling for the surgeon while not impacting the ability of any of the camera devices to detect and track objects.

The lighting component may include a plurality of lights, the plurality of lights fixed with respect to the surgical field. The plurality of lights may be scialytic lights. The camera device may be an infrared depth camera, which may capture infrared images or image information (e.g., from reflectors on a tracked object). The lighting component may be secured within a housing, and a ceiling mounted arm may be connected to the housing or a mobile cart.

Figure 5:
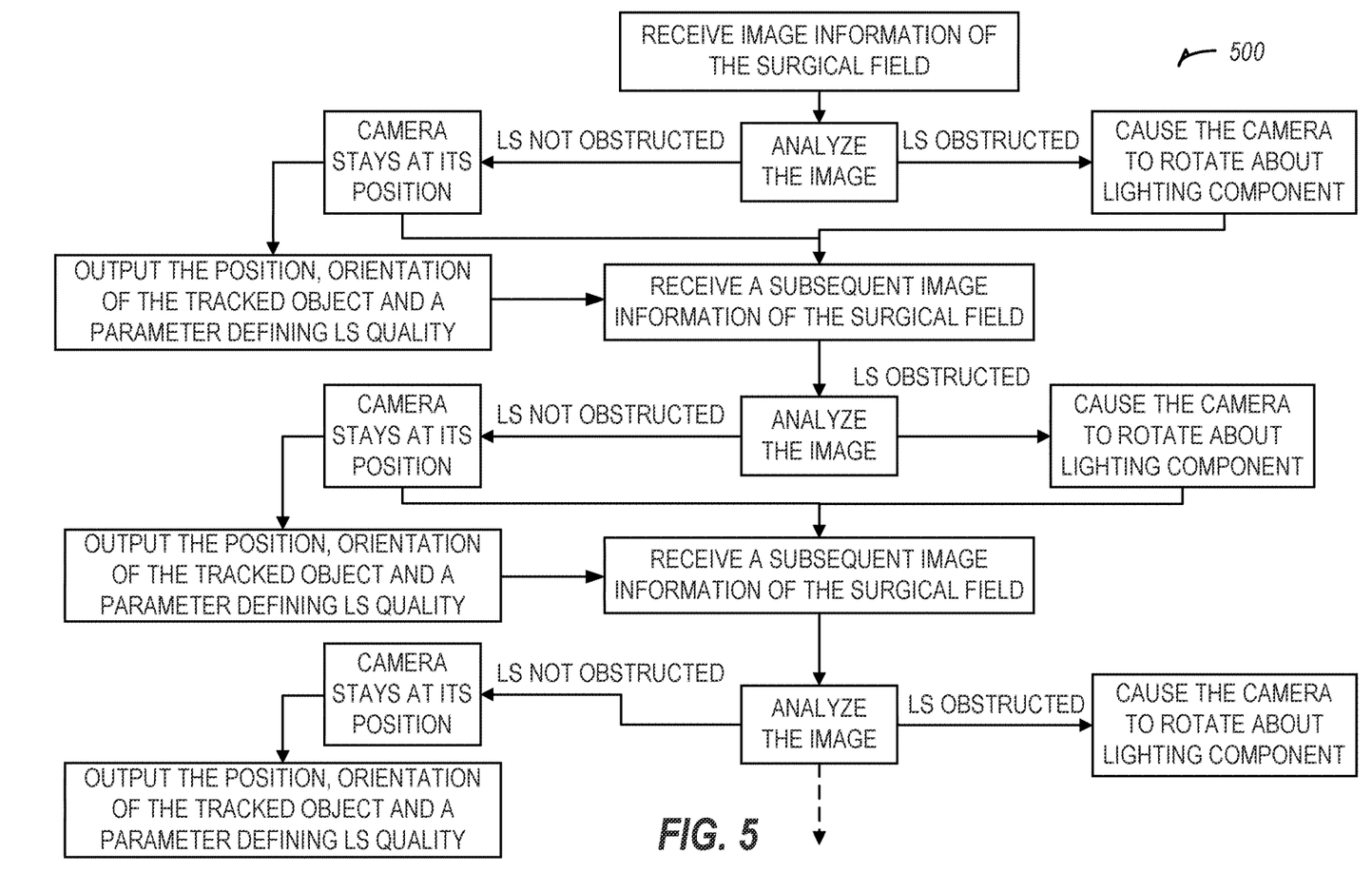
FIG. 5 illustrates a flowchart for scialytic light navigation in accordance with some embodiments.

FIG. 5 illustrates a flowchart 500 for scialytic light navigation in accordance with some embodiments. The flowchart 500 illustrates iteratively analyzing images captured by a camera to determine whether a line of sight (LS) to a tracked object is obstructed or not obstructed. In response to determining the LS is obstructed, the flowchart 500 includes causing the camera to rotate about the lighting component. In response to determining that the LS is not obstructed, the flowchart 500 includes retaining the camera at its position, and outputting the position or orientation of the tracked object. The flowchart 500 may output a parameter defining LS quality (e.g., an amount the LS is obstructed, an indication of whether or to what degree the LS is like to be obstructed, or the like).

In the example shown in flowchart 500, the camera takes a first image. This image is analyzed to determine if the LS is obstructed or not. If the LS is not obstructed, the flowchart 500 includes outputting the position and orientation of the tracked object, as well as optionally a parameter defining LS quality. If the LS is obstructed, the camera may rotate (the amplitude may correspond to the parameter defining obstruction). After rotating, the camera takes another image. This image is then analyzed to determine if line of sight is still obstructed. If LS is still obstructed, the camera moves and the operations may be repeated until the LS is not obstructed. If the LS is not obstructed the system outputs position and orientation of the tracked object and the parameter defining LS quality.

Figure 6:
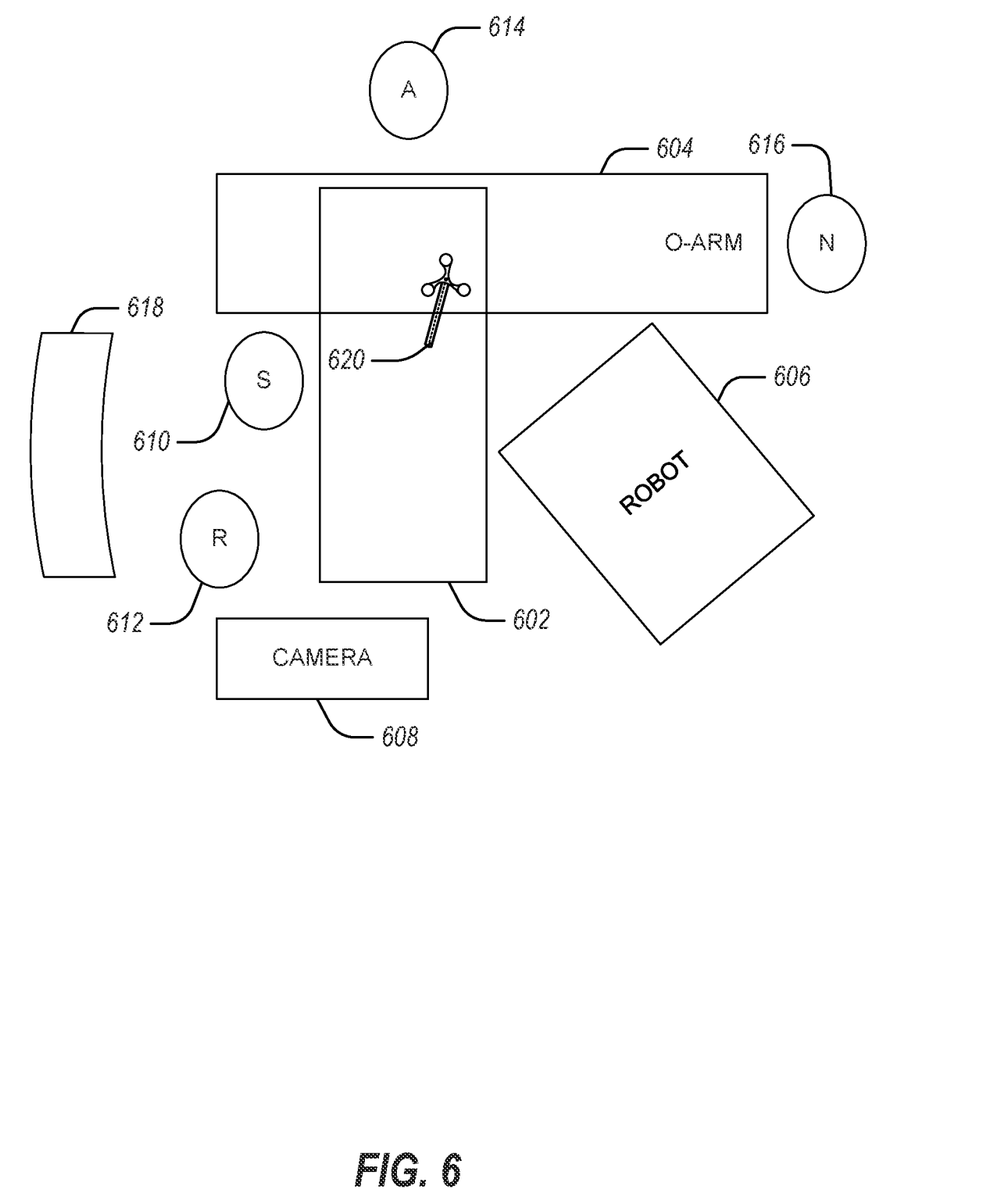
FIG. 6 illustrates an example simulation of an overhead view of a surgical field in accordance with some embodiments.

FIG. 6 illustrates an example simulation 600 of an overhead view of a surgical field in accordance with some embodiments. The simulation 600 is a visual example that may be used in determining an initial line of sight (or example lines of sight). The simulation 600 may include a table 602, an operating arm 604, a robot 606, a camera 608, and one or more people (e.g., a surgeon 610, a resident 612, an anesthesiologist 614, or a nurse 616) or other objects (e.g., a display screen 618). In an example, a user (e.g., a surgeon) may arrange the simulation 600 to look like the user's surgical field. The components of the simulation 600 may be moved or arranged by the user or may be placed automatically by a processor running the simulation 600. In an example, objects (e.g., the table 602) may be static and other objects (e.g., the robot 606 or the surgeon 610) may be moveable.

The simulation 600 may include a tracked object 620 (e.g., passive or active) for determining a line of sight to the camera 608. The simulation 600 may try different lines of sight corresponding to different rotations of the camera 608 (e.g., around a lighting component as discussed above) to determine a best or initial line of sight. The simulation 600 may cause objects that are moveable to move and recalculate a best or initial line of sight. In an example, the simulation 600 may determine one or more locations or orientations of various objects within the simulation 600 that cause the camera 608 to have fewer or more lines of sight to the tracked object 620. The arrangements with fewer lines of sight may be identified to the user so that these may be avoided during an actual surgical procedure. For example, the simulation 600 may move the robot 606 to where the resident 612 is in FIG. 6, and determine that this leads to fewer lines of sight (or an increase in lost line of sight). The position or orientation of the robot 606 may then be output, such as to a display screen to warn the user to avoid placing the robot in the position where the resident 612 is in FIG. 6.

In another example, at the beginning of a surgical procedure, a camera may rotate 360° around the lighting component to find the position relative to the best line of sight (e.g., without needing the simulation 600 or to verify or validate findings of the simulation 600). In this example, the best line of sight may be determined by using a parameter defining line of sight such as tracked object volume or amount of light received. To do this the surgeon may manually position an object to be tracked above the surgical table/field and trigger a calibration procedure. During the surgical procedure the camera may always be looking for the best line of sight. The best line of sight may be defined as a line of sight that provides the most accurate tracking.

Figure 7:
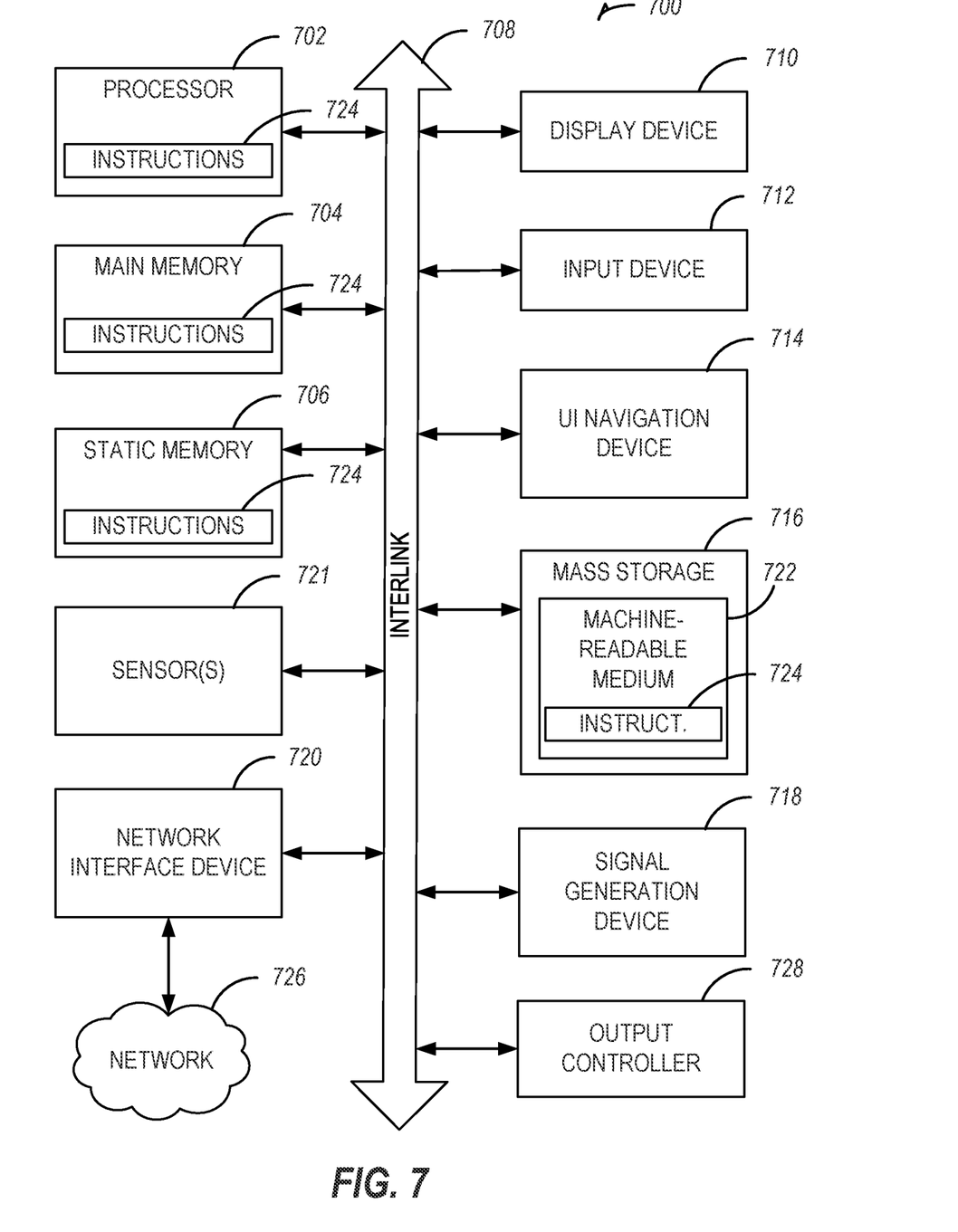
FIG. 7 illustrates a block diagram of an example machine upon which any one or more of the techniques discussed herein may perform in accordance with some embodiments.

FIG. 7 illustrates a block diagram of an example machine 700 upon which any one or more of the techniques discussed herein may perform in accordance with some embodiments. In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710, an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., Universal Serial Bus (USB), parallel, or other wired or wireless (e.g., infrared (IR), near field communication (NFC), etc) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine readable medium 722 is illustrated as a single medium, the term "machine readable medium" may include a single medium or multiple media (e.g., a centralized or distributed database, and/or associated caches and servers) configured to store the one or more instructions 724. The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine readable medium examples may include solid-state memories, and optical and magnetic media.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

VARIOUS NOTES & EXAMPLES

Each of these non-limiting examples may stand on its own, or may be combined in various permutations or combinations with one or more of the other examples.

Example 1 is a system for tracking an object within a surgical field, the system comprising: a lighting component to illuminate a surgical field; a camera device coupled to the lighting component via a rotational component configured to rotate the camera device with respect to the lighting component; a computing system communicatively coupled to the camera device, the computing system including a processor and a memory device, the memory device including instructions that, when executed by the processor, cause the computing system to: receive, from the camera device, first image information of the surgical field; analyze the first image information to detect that a sight line from the camera device to a tracked object is at least partially obstructed; control the rotational component to rotate the camera device about the lighting component; receive, from the camera device subsequent to the camera device rotating, second image information of the surgical field indicative of a position and orientation of the tracked object within the surgical field; and output the position and the orientation of the tracked object.

In Example 2, the subject matter of Example 1 includes, wherein the rotational component is configured to rotate the camera device to a location where the tracked object is not obstructed in a second sight line to the camera device without the lighting component rotating.

In Example 3, the subject matter of Examples 1-2 includes, wherein the lighting component includes a plurality of lights, the plurality of lights fixed with respect to the surgical field.

In Example 4, the subject matter of Example 3 includes, wherein the plurality of lights are scialytic lights.

In Example 5, the subject matter of Examples 1-4 includes, a second camera device coupled to the lighting component via the rotational component.

In Example 6, the subject matter of Example 5 includes, wherein the computing device is to control the rotational component to rotate the camera device about the lighting component in response to determining that the tracked object is at least partially obstructed from the sight line of the camera device and a second sight line of the second camera device.

In Example 7, the subject matter of Examples 1-6 includes, wherein the camera device is an infrared depth camera.

In Example 8, the subject matter of Examples 1-7 includes, wherein the system further includes a motor to cause the rotational component to rotate.

In Example 9, the subject matter of Examples 1-8 includes, wherein the system further includes a housing or a mobile cart, including the lighting component, and a ceiling mounted arm connected to the housing or mounted arm connected to the mobile cart.

In Example 10, the subject matter of Examples 1-9 includes, wherein the computing device is further to cause a light of the lighting component to flash in response to detecting the at least partial obstruction.

In Example 11, the subject matter of Examples 1-10 includes, wherein to control the rotational component to rotate the camera device about the lighting component, the computing device is to control the rotational component to constantly rotate the camera device.

Example 12 is a lighting fixture comprising: a lighting component to illuminate a surgical field; a rotational component configured to rotate with respect to the lighting component; a camera device configured to: couple to the rotational component to rotate with respect to the lighting component; and capture an image of a tracked device within the surgical field.

Example 13 is a computer implemented method for tracking an object within a surgical field, the method comprising: receiving, at a processor from a camera device, first image information of the surgical field; analyzing, using the processor, the first image information to detect that a sight line from the camera device to a tracked object is at least partially obstructed; communicating a signal to a rotational component associated with the camera device, the signal to rotate the camera device about a lighting component; receiving, from the camera device subsequent to the camera device rotating, second image information of the surgical field indicative of a position and orientation of the tracked object within the surgical field; and outputting, from the processor, the position and the orientation of the tracked object.

In Example 14, the subject matter of Example 13 includes, wherein communicating the signal to rotate the camera device includes calculating a position to rotate the camera device where the tracked object is not obstructed in a second sight line to the camera device without a lighting component rotating.

In Example 15, the subject matter of Examples 13-14 includes, communicating the signal to rotate the camera device includes calculating a position to rotate the camera device in response to determining that the tracked object is at least partially obstructed from the sight line of the camera device and a second sight line of a second camera device.

In Example 16, the subject matter of Examples 13-15 includes, wherein communicating the signal to rotate the camera device includes causing, by the processor, activation of a motor to cause a rotational component coupled to a lighting component to rotate.

In Example 17, the subject matter of Examples 13-16 includes, generating an alert signal to flash a light of a lighting component in response to detecting the at least partial obstruction.

In Example 18, the subject matter of Examples 13-17 includes, wherein communicating the signal to rotate the camera device about a lighting component, includes communicating the signal to constantly rotate the camera device.

Example 19 is at least one non-transitory machine-readable medium including instructions for tracking an object within a surgical field, which when executed by a processor, cause the processor to: receive, from a camera device, first image information of the surgical field; analyze the first image information to detect that a sight line from the camera device to a tracked object is at least partially obstructed; communicating a signal to a rotational component associated with the camera device, the signal to cause the camera device to rotate about a lighting component; receive, from the camera device subsequent to the camera device rotating, second image information of the surgical field indicative of a position and orientation of the tracked object within the surgical field; and output the position and the orientation of the tracked object.

In Example 20, the subject matter of Example 19 includes, wherein to communicate the signal to rotate the camera device, the instructions further cause the processor to calculate a position to rotate the camera device where the tracked object is not obstructed in a second sight line to the camera device without a lighting component rotating.

In Example 21, the subject matter of Examples 19-20 includes, wherein to communicate the signal to rotate the camera device, the instructions further cause the processor to calculate a position to rotate the camera device in response to determining that the tracked object is at least partially obstructed from the sight line of the camera device and a second sight line of a second camera device.

In Example 22, the subject matter of Examples 19-21 includes, wherein to communicate the signal to rotate the camera device, the instructions further cause the processor to cause activation of a motor to cause a rotational component coupled to a lighting component to rotate.

In Example 23, the subject matter of Examples 19-22 includes, wherein the instructions further cause the processor to generate an alert signal to flash a light of a lighting component in response to detecting the at least partial obstruction.

In Example 24, the subject matter of Examples 19-23 includes, wherein to communicate the signal to rotate the camera device about a lighting component, the instructions further cause the processor to communicate the signal to constantly rotate the camera device.

Example 25 is at least one machine-readable medium including instructions that, when executed by processing circuitry, cause the processing circuitry to perform operations to implement of any of Examples 1-24.

Example 26 is an apparatus comprising means to implement of any of Examples 1-24.

Example 27 is a system to implement of any of Examples 1-24.

Example 28 is a method to implement of any of Examples 1-24.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMS), read only memories (ROMs), and the like.

What is claimed is:

1. A system for tracking an object within a surgical field, the system comprising:
   a lighting component to illuminate a surgical field;
   a camera device coupled to the lighting component via a rotational component configured to rotate the camera device 360 degrees around a radial axis centered with respect to the lighting component;
   a computing system communicatively coupled to the camera device, the computing system including a processor and a memory device, the memory device including instructions that, when executed by the processor, cause the computing system to:
   receive, from the camera device, first image information of the surgical field;
   analyze the first image information to detect that a sight line from the camera device to a tracked object is at least partially obstructed;
   control the rotational component to rotate the camera device about the lighting component.

2. The system of claim 1, wherein the rotational component is configured to rotate the camera device to a location where the tracked object is not obstructed in a second sight line to the camera device without the lighting component rotating.

3. The system of claim 1, wherein the lighting component includes a plurality of lights, the plurality of lights fixed with respect to the surgical field.

4. The system of claim 3, wherein the plurality of lights are scialytic lights.

5. The system of claim 1, further comprising a second camera device coupled to the lighting component via the rotational component.

6. The system of claim 5, wherein the computing device is to control the rotational component to rotate the camera device about the lighting component in response to determining that the tracked object is at least partially obstructed from the sight line of the camera device and a second sight line of the second camera device.

7. The system of claim 1, wherein the camera device is an infrared depth camera.

8. The system of claim 1, wherein the system further includes a motor to cause the rotational component to rotate.

9. The system of claim 1, wherein the system further includes a housing, including the lighting component, and a ceiling mounted arm connected to the housing.

10. The system of claim 1, wherein the computing device is further to cause a light of the lighting component to flash in response to detecting the at least partial obstruction.

11. The system of claim 1, wherein to control the rotational component to rotate the camera device about the lighting component, the computing device is to control the rotational component to constantly rotate the camera device.

12. A computer implemented method for racking an object within a surgical field, the method comprising:
    receiving, at a processor from a camera device, first image information of the surgical field;
    analyzing, using the processor, the first image information to detect that a sight line from the camera device to a tracked object is at least partially obstructed;
    communicating a signal to a rotational component associated with the camera device, the signal to rotate the camera device about a radial axis centered on a lighting component;
    receiving, from the camera device subsequent to the camera device rotating, second image information of the surgical field indicative of a position and orientation of the tracked object within the surgical field; and
    outputting, from the processor, the position and the orientation of the tracked object.

13. The method of claim 12, wherein communicating the signal to rotate the camera device includes calculating a position to rotate the camera device where the tracked object is not obstructed in a second sight line to the camera device without a lighting component rotating.

14. The method of claim 12, wherein communicating the signal to rotate the camera device includes calculating a position to rotate the camera device in response to determining that the tracked object is at least partially obstructed from the sight line of the camera device and a second sight line of a second camera device.

15. The method of claim 12, wherein communicating the signal to rotate the camera device includes causing, by the processor, activation of a motor to cause the rotational component coupled to the lighting component to rotate.

16. The method of claim 12, further generating an alert signal to flash a light of the lighting component in response to detecting the at least partial obstruction.

17. The method of claim 12, wherein communicating the signal to rotate the camera device about the lighting component, includes communicating the signal to constantly rotate the camera device.

18. At least one non-transitory machine-readable medium including instructions for tracking an object within a surgical field, which when executed by a processor, cause the processor to:

receive, from a camera device, first image information of the surgical field;

analyze the first image information to detect that a sight line from the camera device to a tracked object is at least partially obstructed;

communicating a signal to a rotational component associated with the camera device, the signal to cause the camera device to rotate about a radial axis centered on a lighting component, wherein the signal causes the rotational component to rotate the camera device within +/−180 degrees about the radial axis from an initial position;

receive, from the camera device subsequent to the camera device rotating, second image information of the surgical field indicative of a position and orientation of the tracked object within the surgical field; and output the position and the orientation of the tracked object.

19. The at least one machine-readable medium of claim 18, wherein to communicate the signal to rotate the camera device, the instructions further cause the processor to calculate a position to rotate the camera device where the tracked object is not obstructed in a second sight line to the camera device without a lighting component rotating.

20. The at least one machine-readable medium of claim 18, wherein to communicate the signal to rotate the camera device, the instructions further cause the processor to calculate a position to rotate the camera device in response to determining that the tracked object is at least partially obstructed from the sight line of the camera device and a second sight line of a second camera device.

* * * * *

UNITED STATES PATENT AND TRADEMARK OFFICE
CERTIFICATE OF CORRECTION

PATENT NO. : 11,438,499 B2
APPLICATION NO. : 17/232756
DATED : September 6, 2022
INVENTOR(S) : Florian Coiseur It is certified that error appears in the above-identified patent and that said Letters Patent is hereby corrected as shown below:

In the Claims

In Column 16, Line 29, in Claim 12, delete "racking" and insert --tracking-- therefor Signed and Sealed this
Twenty-fifth Day of October, 2022

*Katherine Kelly Vidal*

Katherine Kelly Vidal
*Director of the United States Patent and Trademark Office*